United States Patent
Tan et al.

(10) Patent No.: US 8,153,812 B1
(45) Date of Patent: Apr. 10, 2012

(54) TWO-PHOTON ABSORBING DIPHENYLAMINOFLUORENE-BENZOTHIAZOLE BIS(AMINOPHENOXY) MONOMERS

(75) Inventors: Loon-Seng Tan, Centerville, OH (US); Ramamurthi Kannan, Cincinnati, OH (US); Matthew J. Dalton, Bellbrook, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 13/032,735

(22) Filed: Feb. 23, 2011

Related U.S. Application Data

(60) Provisional application No. 61/307,036, filed on Feb. 23, 2010.

(51) Int. Cl.
C07D 277/66 (2006.01)
(52) U.S. Cl. ........................................ 548/160
(58) Field of Classification Search .................. 548/160
See application file for complete search history.

(56) References Cited

U.S. PATENT DOCUMENTS

| | | | |
|---|---|---|---|
| 6,300,502 B1 | 10/2001 | Kannan et al. | |
| 6,555,682 B1 | 4/2003 | Kannan et al. | |
| 6,730,793 B1 | 5/2004 | Kannan et al. | |
| 6,867,304 B1 | 3/2005 | Tan et al. | |
| 7,067,674 B1 | 6/2006 | Kannan et al. | |
| 7,319,151 B1 | 1/2008 | Tan et al. | |

OTHER PUBLICATIONS

Dalton, Matthew J.; Kannan, Ramamurthi; Jakubiak, Rachel; Haley, Joy E.; Tan, Loon-Seng. "Synthesis and characterization of novel aromatic imide polymer and co-polymers containing diphenylaminofluorene-benzothiazole as two-photon chromophoric units." Polymer Preprints (American Chemical Society, Division of Polymer Chemistry) (2009), 50(1), 495-496.

Jhaveri, Shalin J.; McMullen, Jesse D.; Sijbesma, Rint; Tan, Loon-Seng; Zipfel, Warren; Ober, Christopher K. Direct Three-Dimensional Microfabrication of Hydrogels via Two—Photon Lithography in Aqueous Solution. Chemistry of Materials (2009), 21(10), 2003-2006.

Rogers, Joy E.; Slagle, Jonathan E.; McLean, Daniel G.; Sutherland, Richard L.; Brant, Mark C.; Heinrichs, James; Jakubiak, Rachel; Kannan, Ramamurthi; Tan, Loon-Seng; Fleitz, Paul A. Insight into the Nonlinear Absorbance of Two Related Series of Two—Photon Absorbing Chromophores. Journal of Physical Chemistry A (2007), 111(10), 1899-1906.

He, Guang S.; Tan, Loon-Seng; Zheng, Qingdong; Prasad, Paras N. Multiphoton Absorbing Materials: Molecular Designs, Characterizations, and Applications. Chemical Reviews (Washington, DC, United States) (2008), 108(4), 1245-1330.

Kannan, Ramamurthi; He, Guang S.; Lin, Tzu-Chau; Prasad, Paras N.; Vaia, Richard A.; Tan, Loon-Seng. Toward Highly Active Two-Photon Absorbing Liquids. Synthesis and Characterization of 1,3,5-Triazine-Based Octupolar Molecules. Chemistry of Materials (2004), 16(1), 185-194.

He, Guang S.; Lin, Tzu-Chau; Dai, Jianming; Prasad, Paras N.; Kannan, Ramamurthi; Dombroskie, Ann G.; Vaia, Richard A.; Tan, Loon-Seng. Degenerate two-photon-absorption spectral studies of highly two-photon active organic chromophores. Journal of Chemical Physics (2004), 120(11), 5275-5284.

Kannan, Ramamurthi; He, Guang S.; Yuan, Lixiang; Xu, Faming; Prasad, Paras N.; Dombroskie, Ann G.; Reinhardt, Bruce A.; Baur, Jeffery W.; Vaia, Richard A.; Tan, Loon-Seng. Diphenylaminofluorene-Based Two-Photon-Absorbing Chromophores with Various π-Electron Acceptors. Chemistry of Materials (2001), 13(5), 1896-1904.

Siwy, Mariola; Jarzabek, Bozena; Switkowski, Krzysztof; Pura, Bronislaw; Schab-Balcerzak, Ewa. Novel poly(esterimide)s containing a push-pull type azobenzene moiety-synthesis, characterization and optical properties. Polymer Journal (Tokyo, Japan) (2008), 40(9), 813-824.

*Primary Examiner* — Laura L. Stockton

(74) *Attorney, Agent, or Firm* — AFMCLO/JAZ; Bart Hersko

(57) ABSTRACT

Provided are new 2PA chromophores of the formula:

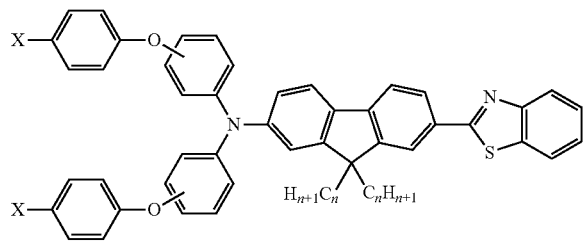

wherein X=para- or meta-$NO_2$; para- or meta-$NH_2$; and $C_nH_{n+1}$ is either a straight or branched alkyl chain, and n is an integer from 1-20.

2 Claims, No Drawings

TWO-PHOTON ABSORBING DIPHENYLAMINOFLUORENE-BENZOTHIAZOLE BIS(AMINOPHENOXY) MONOMERS

CROSS REFERENCE TO RELATED APPLICATION

This application claims priority of the filing date of provisional application Ser. No. 61/307,036 filed Feb. 23, 2010.

RIGHTS OF THE GOVERNMENT

The invention described herein may be manufactured and used by or for the Government of the United States for all governmental purposes without the payment of any royalty.

BACKGROUND OF THE INVENTION

The present invention relates to chromophores with large, effective two-photon absorption cross-sections.

Two-photon or multiphoton absorption occurs through the simultaneous absorption of two or more photons via virtual states in an absorbing medium, with the former being more common. For a given chromophore, these absorption processes take place at wavelengths much longer than the cut-off wavelength of its linear (single-photon) absorption. In the case of two-photon absorption (2PA), two quanta of photons may be absorbed from a single light source (degenerate 2PA) or two sources of different wavelengths (non-degenerate 2PA). Although multiphoton absorption processes have been theoretically described in 1931 and experimentally confirmed about 30 years later, this field remained dormant largely due to the lack of materials with sufficiently large two-photon sensitivity, quantified as two-photon cross-section ($\sigma_2'$), which is usually expressed in the units of Göppert-Mayer (1 GM=$10^{-50}$ $cm^4 \cdot s \cdot photon^{-1} \cdot molecule^{-1}$). Then, in the mid-1990s, several new classes of chromophores exhibiting very large effective $\sigma_2'$ values were reported. In conjunction with the increased availability of ultrafast high-intensity lasers, the renewed interest has not only sparked a flurry of activities in the preparation of novel dye molecules with enhanced $\sigma_2'$ values, but also in advancing many previously conceived applications based on 2PA process in photonics and biophotonics, which are now enabled by these new chromophores. It is important to recognize the following useful features of the 2PA phenomenon based on the fact that 2PA scales nonlinearly with the squared intensity of the incident laser beam: (a) upconverted emission, whereby an incident light at lower frequency (energy) can be converted to an output light at higher frequency, for instance, near infrared (NIR) to ultraviolet (UV) upconversion; (b) deeper penetration of incident NIR light (into tissue samples, for example) than UV light that also may be hazardous with prolonged exposure; (c) highly localized excitation as compared with one-photon processes allowing for precise spatial control of in situ photochemical or photophysical events in the absorbing medium, thereby minimizing undesirable activities such as photodegradation or photobleaching; and (d) fluorescence, when properly manipulated, that would allow for information/signal feedback or amplification in conjunction with other possible, built-in effects such as surface plasmonic enhancement. It is anticipated that further ingenious utilization of these basic characteristics will lead to practical applications other than the ones that have already emerged in such diverse areas as bio-medical fluorescence imaging, data storage, protection against accidental laser damage, microfabrication of microelectromechanical systems (MEMS), photodynamic therapy, etc. In the past decade or so, significant advances have been made in the fundamental understanding of general structure-property relationship that has led to the design and synthesis of two-photon absorbers with very large cross-section values. Although further enhancement of 2PA cross-section is still possible as suggested by a number of theoretical studies, for certain applications, the two-photon-property requirement has essentially been met by the state-of-art chromophores. Because of the possible property-processing/fabrication trade-off, the secondary properties, e.g. thermal and mechanical properties, which are important to material processing into various useful forms (films, coatings, fibers, windows etc.) and configurations, should be addressed. For the aforementioned solid forms, polymers can offer many advantages such as the flexibility in fine-tuning the material properties and the availability of many processing options.

Accordingly, it is an object of the present invention to provide new two-photon absorbing aromatic diamines, which contain electron-donating triarylalkylamine and electron-accepting benzothiazole, and are useful monomers in the preparation of high performance polymers such as polyimides, polyamides and poly(amide-imides) for nonlinear optical applications.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

The general synthetic scheme of the dinitro precursors and the corresponding diamino monomers is depicted in Scheme 1. It is known that aromatic diamines can serve as the common co-monomers for polyimide, polyamides, and poly (amide-imides). In addition, the parent compound (2a, R=H, see Scheme 1) designated as AF-240 has a relatively high effective two-photon cross-section (effective (nanosecond) $\sigma_2'$ value of 9,800 GM at 800 nm) and a number of structurally related, monofunctionized (see U.S. Pat. No. 7,067,674) and difunctionalized (see U.S. Pat. No. 7,319,151) derivatives are also highly two-photon active. Based on this structural motif and together with the molecular symmetry consideration to avoid unequal reactivity, the required diamines in the present invention were designed with functionalization taking place at the 3,3'- and 4,4'-positions of the diphenylamino (donor) segment of AF240. The important intermediates to the targeted momoners, namely the 3,3'-bis(phenol) and 4,4'-bis (phenol), compounds 4c and 4 d respectively in Scheme 1, were synthesized via (i) a Pd-catalyzed amination from the fluorenyl bromide 1 and 3,3'-dimethoxydiphenylamine or 4,4'-dimethoxydiphenylamine, followed by (ii) demethylation with liquid pyridinium chloride. The diamino monomer was synthesized from the (iii) double aromatic substitution reaction of 3a or 3b and 4-fluoro-1-nitrobenzene in the presence of potassium carbonate, followed by (iv) catalytic reduction with dihydrogen or hydrazine hydrate.

Scheme 1: Synthesis of dinitro intermediates and diamino monomers

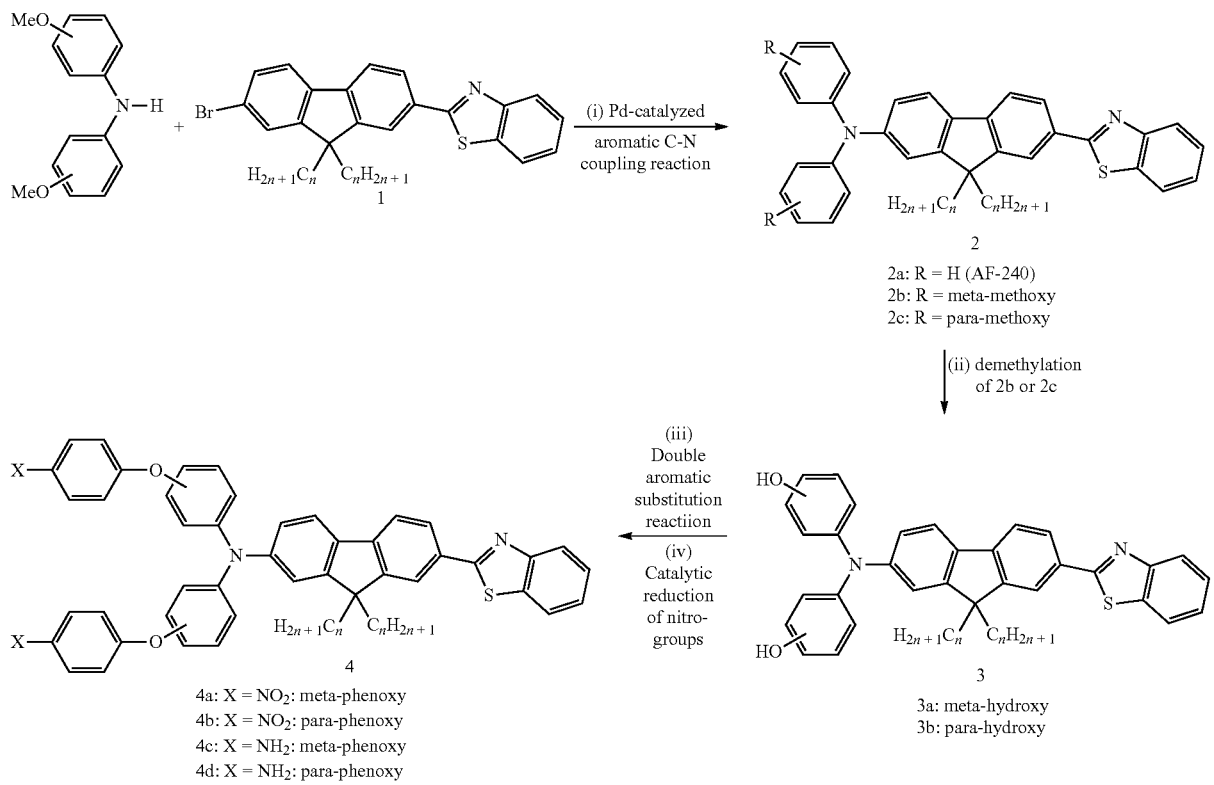

2a: R = H (AF-240)
2b: R = meta-methoxy
2c: R = para-methoxy

3a: meta-hydroxy
3b: para-hydroxy

4a: X = NO$_2$: meta-phenoxy
4b: X = NO$_2$: para-phenoxy
4c: X = NH$_2$: meta-phenoxy
4d: X = NH$_2$: para-phenoxy

SUMMARY OF THE INVENTION

In accordance with the present invention, there are provided new 2PA diamino monomers of the formula:

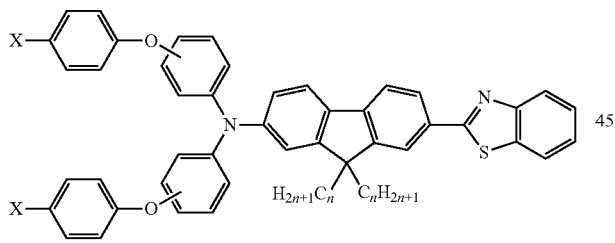

wherein X=NO$_2$ or NH$_2$; and C$_n$H$_{2n+1}$ is either a straight or branched alkyl chain, and n is an integer from 1, to 20, preferably n is from 1 to 10.

The chromophores of this invention can be synthesized following the procedures given in the following Examples which illustrate the invention:

EXAMPLE 1

2,7-Dibromofluorene

To a mechanically stirred mixture of fluorene (113.76 g, 0.68 mol), iodine (1.96 g, 0.0077 mol), and methylene chloride (750 mL), bromine (74 mL, 1.44 mol) diluted with methylene chloride (100 mL) was added dropwise at room temperature over a period of 1.5 hours. After 5 minutes, a solution of sodium bisulfite (15.0 g) in water (100 mL) was added and the mixture was stirred for 30 minutes, when the mixture became colorless. Water (750 mL) was then added, and methylene chloride was distilled off. The product slurry was filtered and the product was air-dried, 220.5 g, m.p. 156-160° C. This material was used in the next step without further purification.

EXAMPLE 2

9,9-Diethyl-2,7-dibromofluorene

To a mechanically stirred mixture of 2,7-dibromofluorene (Example 1; 66.5 g, 0.205 mol) powdered potassium hydroxide (56.0 g, 1.0 mol), potassium iodide (3.4 g) and DMSO (150 mL), cooled to 10° C., ethyl bromide (40 ml, 58.4 g, 0.536 mol) was added dropwise over 45 minutes. The mixture turned from red to light purple. After allowing the temperature to warm to 20° C., the mixture was left overnight to stir and poured into water, 77.0 g. (98.7% yield), m.p. 144-153° C. The product was then recrystallized from hexane (550 mL) with charcoal treatment, and collected in two crops, m.p. 154-157° C. and 153-154° C., totaling 60.36 g. (77.4% yield).

EXAMPLE 3

9,9-Diethyl-7-bromo-fluorene-2-carboxaldehyde

To a mechanically stirred solution of 9,9-diethyl-2,7-dibromofluorene (Example 2; 59.38 g, 0.1563 mol) in THF (325 mL) cooled in dry ice-ethanol bath, n-butyl lithium (104 mL of 1.6M solution in hexanes, 0.1664 mol, 1.06 eq.) was added dropwise over 25 minutes. After 20 minutes, DMF (17 mL, 0.22 mol) in THF (30 mL) was added, and the mixture was stirred in the cooling bath for 1.5 hours, and outside the bath for 1 hour. The reaction was then cooled to 5° C. and treated with hydrochloric acid (12.5 of concentrated hydrochloric acid diluted with 50 mL water). The mixture was diluted with 200 mL of toluene, and the aqueous phase was separated and extracted with 200 mL of toluene. The combined organic phase was washed with dilute sodium bicarbonate solution, dried over magnesium sulfate and concentrated. The residual solids were recrystallized from heptane-ethyl acetate (9:1) mixture, to get colorless solids, 40.29 g (78.4% yield), m.p. 126-128° C. The mother liquor after chromatography over 150 g of silica gel, elution with 1:1 heptane-toluene mixture, and trituration of residual solids in hexanes gave additional product, 6.56 g (12.8% yield, total 91% yield), m.p. 126-128° C. Mass Spec: m/z 328, 330, (M+). A sample for analysis was prepared by recrystallization from hexanes, m.p. 127-129° C. Analysis: Calculated for $C_{18}H_{17}BrO$: C, 65.55%; H, 5.20%; Br, 24.27%. Found: C, 65.60%; H, 5.51%; Br, 24.71%.

EXAMPLE 4

7-(Benzothiazol-2-yl)-9,9-diethyl-2-bromofluorene

A mixture of 9,9-diethyl-7-bromo-fluorene-2-carboxaldehyde (Example 3; 49.35 g, 0.15 mol), 2-aminothiophenol (20 mL, 0.187 mol, 1.25 eq.), and DMSO (110 mL) was heated in an oil bath to a bath temperature of 195° C., held there for 45 minutes, and then poured into water. The separated solids were collected, reslurried in 1:4 acetic acid-water (1000 mL), filtered, and washed with water and dilute sodium bicarbonate solution. These solids, 80.05 g, were then reslurried in hot ethanol (600 mL) cooled and filtered to get the product, 45.69 g, m.p. 133.6-135° C. An additional 6.6 g, m.p. 134.6-135.5° C., was obtained by chromatography of the ethanol filtrate. Total recovery 52.29 g. (80.3% yield). Mass Spec: m/z 433, 435, (M+). Analysis: Calculated for $C_{24}H_{20}BrNS$: C, 66.37%; H, 4.64%; Br, 18.40%; N, 3.23%; S, 7.37%. Found: C, 66.46%; H, 4.52%; Br, 18.54%; N, 3.14%; S, 7.19%.

EXAMPLE 5

N,N-Di(3-methoxyphenyl)-7-(benzothiazol-2-yl)-9,9-diethyl-fluoren-2-amine

A mixture of 7-benzothiazol-2-yl-9,9-diethyl-2-bromofluorene (Example 4; 10.85 g, 25 mmol), 3,3'-dimethoxydiphenylamine (6.87 g, 30 mmol) and toluene (100 mL) was azeotroped dry under nitrogen and cooled. Bis(dibenzylidene acetone)palladium (0) (0.28 g, 0.49 mmol), bis(diphenylphosphino)ferrocene (0.25 g, 0.45 mmol) and sodium-t-butoxide (3.5 g, 36.4 mmol) were then added and the mixture was heated to 100° C. After 24 hours, the mixture was cooled, diluted with toluene and filtered. The filtrate was washed with water, dried and concentrated. The residue was chromatographed over silica gel. Elution with toluene-heptane (3:1) mixture gave the product, which was recrystallized from a mixture of toluene-heptane, m.p. 178-179.5° C., 11.13 g (76% yield). $^1H$ NMR (CDCl$_3$) δ ppm: 0.35-0.41 (t, 6H), 1.91-2.14 (m, 4H), 3.69 (s, 6H), 6.54-6.74, 7.05-7.68, 7.84-8.10 (m, 18H). $^{13}C$ NMR (CDCl$_3$) δ ppm: 8.61, 32.66, 55.18, 56.44 (sp$^3$C), 108.62, 109.77, 116.66, 119.16, 119.42, 121.00, 121.44, 121.52, 122.94, 123.77, 124.95, 126.28, 127.28, 129.82, 131.55, 134.91, 135.61, 144.48, 147.84, 148.94, 150.67, 151.99, 154.24, 160.46, 168.81 (sp$^2$C). Anal. Calcd for $C_{38}H_{34}N_2O_2S$: C, 78.33%; H, 5.88%; N, 4.81%; S, 5.49%. Found: C, 78.26%; H, 5.96%; N, 4.68%; S 5.47%.

EXAMPLE 6

N,N-Di(3-hydroxyphenyl)-7-(benzothiazol-2-yl)-9,9-diethyl-fluoren-2-amine

A mixture of N,N-di(3-methoxyphenyl)-7-(benzothiazol-2-yl)-9,9-diethyl-fluoren-2-amine (Example 5; 1 g), and pyridine hydrochloride (10 g) was held at 200° C. in an oil bath for 10 hours, cooled, slurried in water, and the red solids were collected. These were slurried in dilute ammonium hydroxide to get the greenish yellow solid product, 1.13 g, m.p. 314-316° C. EIMS: m/z 554 (M+). Anal. Calcd for $C_{36}H_{30}N_2O_2S$: C, 77.95%; H, 5.45%; N, 5.05%; S, 5.78%. Found: C, 77.74%; H, 5.39%; N, 4.83%; S, 5.78%.

EXAMPLE 7

N,N-Di[3-(4-nitrophenoxy)phenyl]-7-(benzothiazol-2-yl)-9,9-diethyl-fluoren-2-amine A mixture of N,N-di(3-hydroxyphenyl)-7-(benzothiazol-2-yl)-9,9-diethyl-fluoren-2-amine (Example 6; 2.94 g, 5.3 mmol), 4-nitrofluorobenzene (2.56 g, 20 mmol), potassium carbonate (2.29 g, 16.6 mmol) and DMAc (27 mL) was held at 97° C. for 5 hr, and then poured into water. The separated solids (4.38 g) were transferred to a column of silica gel and eluted with toluene to get the product, 4.12 g (97% yield), m.p. 200-201° C. Recrystallization from a toluene-heptane mixture provided a purer sample with m.p. 202-203° C. $^1H$ NMR (400 MHz, CDCl$_3$) δ ppm: 8.15-8.22 (m, 4H), 8.07-8.12 (m, 2H), 8.02 (dd, $J_1$=7.9 Hz, $J_2$=1.6 Hz, 1H), 7.91 (d, J=7.9 Hz, 1H), 7.72 (d, J=7.9 Hz, 1H), 7.68 (d, J=8.1 Hz, 1H), 7.45-7.55 (m, 1H), 7.36-7.42 (m, 1H), 7.31 (t, J=8.1 Hz, 2H), 7.12-7.2 (m, 2H), 6.98-7.05 (m, 6H), 6.89 (t, J=2.2 Hz, 2H), 6.72-6.77 (m, 2H), 1.88-2.15 (m, 4H), 0.31 (t, J=7 Hz, 6H); $^{13}C$ NMR (100 MHz, CDCl$_3$) δ ppm: 168.52, 162.96, 155.53, 154.15, 152.45, 150.66, 149.23, 146.49, 143.77, 142.63, 137.09, 134.90, 132.07, 130.83, 127.32, 126.31, 125.90, 125.05, 124.54, 122.97, 121.55, 121.47, 121.40, 120.19, 120.09, 119.73, 117.00, 115.47, 114.66, 56.49, 32.61, 8.55. MS (m/z): 796 (M+). Anal. Calcd. for $C_{48}H_{36}N_4O_6S$: C, 72.35%; H, 4.55%; N, 7.03%; S, 4.02%. Found: C, 72.15%; H, 4.87%; N, 6.87%; S, 3.95%.

EXAMPLE 8

N,N-Di[3-(4-aminophenoxy)phenyl]-7-(benzothiazol-2-yl)-9,9-diethyl-fluoren-2-amine To a solution of N,N-di[3-(4-nitrophenoxy)phenyl]-7-(benzothiazol-2-yl)-9,9-diethyl-fluoren-2-amine (Example 7; 13.68 g, 17.2 mmol) in 300 mL of 1/1 tetrahydrofuran/ethanol mixture under argon was added 10% palladium/carbon (500 mg). The mixture was heated to 60° C., and hydrazine hydrate (12.7 mL, ~206 mmol) was added slowly over 40 min by addition funnel. The solution became dark, fluorescent green and, after 8 hr, was cooled to room temperature and poured into 1.5 L of distilled water. After a few hours of stirring to evaporate some THF, a fine yellow solid was filtered and purified by column chromatography eluting with ethyl acetate/toluene. The product was further slurried in 100 mL of hot EtOH, filtered at room temperature, and dried in vacuo at 70° C. overnight to give 8.4 g (65%). $^1H$ NMR (400 MHz, CDCl$_3$) δ ppm: 8.08 (m, 2H), 8.01 (dd, $J_1$=8 Hz, $J_2$=1.6

Hz, 1H), 7.91 (d, J=8 Hz, 1H), 7.70 (d, J=8 Hz, 1H), 7.48-7.55 (m, 1H), 7.35-7.42 (m, 1H), 7.05-7.18 (m, 4H), 6.52-6.59 (m, 2H), 3.5-3.6 (br. s, 4H), 1.95-2.15 (m, 4H), 0.34 (t, J=7 Hz, 6H); $^{13}$C NMR (100 MHz, CDCl$_3$) δ ppm: 168.97, 159.73, 154.38, 152.23, 150.91, 149.04, 148.61, 147.69, 144.56, 142.72, 135.98, 135.07, 131.71, 129.98, 127.39, 126.42, 125.11, 124.19, 123.08, 121.68, 121.59, 121.19, 121.00, 119.60, 119.54, 117.90, 116.31, 113.33, 111.70, 56.57, 32.77, 8.73; MS (m/z): 736 (M$^+$); Anal. Calcd. for C$_{48}$H$_{40}$N$_4$O$_2$S: C, 78.23%; H, 5.47%; N, 7.60%; S, 4.35%%. Found: C, 78.01%%; H, 5.60%%; N, 7.62%%; S, 4.31%.

EXAMPLE 9

N,N-Di(4-methoxyphenyl)-7-(benzothiazol-2-yl)-9,9-diethyl-fluoren-2-yl)-amine

A mixture of 7-(benzothiazol-2-yl)-9,9-diethyl-2-bromofluorene (Example 4; 10.14 g, 23.4 mmol), 4,4'-dimethoxydiphenylamine (Alpha Aesar, 5.26 g, 23.0 mmol), and toluene (100 mL) was azeotroped dry under nitrogen and cooled. Palladium(II) acetate (84.3 mg, 0.375 mmol), bis(dibenzylidene acetone)palladium(0) (228.3 mg, 0.412 mmol) and sodium t-butoxide (2.53 g, 26.3 mmol) were then added, and the reaction mixture was held at 96° C. for 20 hours. After cooling, the mixture was diluted with toluene, and the solution was washed with water, dried and concentrated. The residue (13.6 g) was chromatographed over silica gel, and the column was eluted with toluene to get the product, which was crystallized from a mixture of toluene and heptane, 11.6 g (84% yield), m.p. 187-189° C. The second run of the synthesis under similar conditions led to isolation of the product with m.p. 190.1-192.6° C., and in yield 79%. Mass spec: m/z 582 (M$^+$). Anal. Calcd for C$_{38}$H$_{34}$N$_2$O$_2$S: C, 78.33%; H, 5.88%; N, 4.81%; S, 5.49%. Found: C, 78.38%; H, 6.00%; N, 4.70%; S, 5.30%. $^1$H NMR (CDCl$_3$) δ ppm: 0.38 (t, 6H, 7.3 Hz), 1.8-1.93 (m, 2H), 2.04-2.09 (m, 2H), 3.79 (s, 6H), 6.83-6.85 (m, 4H), 6.90-6.93 (m, 1H), 7.09 (d, 4H, 8.8 Hz), 7.33 (t, 1H, 7.7 Hz), 7.46 (t, 1H, 7.5 Hz), 7.52 (d, 1H, 8.3 Hz), 7.63 (d, 1H, 7.90 Hz), 7.86 (d, 1H, 7.92 Hz), 7.97 (d, 1H, 8.0 Hz), 8.06 (d, 2H, 6.92 Hz). $^{13}$C NMR (CDCl$_3$) δ ppm: 8.74, 32.73, 55.55, 56.37 (4 sp$^3$C), 114.75, 115.70, 119.07, 120.36, 120.88, 121.42, 121.60, 122.94, 124.96, 126.31, 126.36, 127.36, 131.04, 133.53, 134.97, 141.24, 144.93, 149.23, 150.52, 152.11, 154.34, 155.81, and 169.05 (23 sp$^2$C).

EXAMPLE 10

N,N-Di(4-hydroxyphenyl)-7-(benzothiazol-2-yl)-9,9-diethyl-fluoren-2-amine

A mixture of N,N-di(4-methoxyphenyl)-7-(benzothiazol-2-yl)-9,9-diethyl-fluoren-2-amine, (Example 9; 11.0 g, 18.9 mmol), 2-aminothiophenol (9.0 mL, 10.53 g, 84.0 mmol), potassium carbonate (0.58 g, 4.2 mmol) and 1-methylpyrrolidine-2-one (NMP, 50 mL) was heated to 195° C., and held at this temperature for 6 hours. After cooling, the mixture was poured into a mixture of acetic acid (100 mL) and water (750 mL). The separated solids were collected and reslurried in a mixture of ethanol (100 mL) and toluene (50 mL), and the insoluble solids, 7.44 g, m.p. 294-297° C. were collected. Additional 2.71 g, with the same melting point was obtained by concentration of the filtrate, and slurrying the crude product in toluene. Total product recovered was 10.15 g (97% yield). A sample for analysis was prepared by heating 1 g of the sample with 2:1 acetic-acid-water mixture (75 mL), 0.98 g, m.p. 294.2-294.5° C. Mass spec: m/z 554 (M$^+$). Anal. Calcd for C$_{36}$H$_{30}$N$_2$O$_2$S: C, 77.95%; H, 5.45%; N, 5.05%; S, 5.78%. Found; C, 77.95%; H, 5.53%; N, 5.18%; S, 5.90%. $^1$H NMR (DMSO-d$_6$) δ ppm: 0.30 (t, 6H, 7.3 Hz), 1.80-1.84 (m, 2H), 1.99-2.04 (m, 2H), 6.70-6.81 (m, 6H), 6.94-6.97 (m, 4H), 7.42-7.46 (m, 1H), 7.52-7.56 (m, 1H), 7.65 (d, 1H, 8.4 Hz), 7.78 (d, 1H, 7.92 Hz), 7.97-8.13 (m, 4H), 9.38 (s, 2H). $^{13}$C NMR (DMSO-d$_6$) δ ppm: 8.96, 32.23, 56.01 (3 sp$^3$C), 113.42, 116.71, 118.47, 119.66, 121.28, 121.77, 122.68, 123.02, 125.69, 127.06, 127.42, 127.59, 130.52, 131.90, 134.77, 139.22, 145.09, 150.09, 150.34, 151.87, 154.15, 154.50, and 169.38 (23 sp$^2$C).

EXAMPLE 11

N,N-Di[4-(4-nitrophenoxy)phenyl]-7-(benzothiazol-2-yl)-9,9-diethyl-fluoren-2-amine A mixture of N,N-di(4-hydroxyphenyl)-7-(benzothiazol-2-yl)-9,9-diethyl-fluoren-2-amine (Example 10; 8.31 g, 15.0 mmol), 4-nitrofluorobenzene (6.34 g, 44.93 mmol), potassium carbonate (6.30 g, 45.6 mmol) and DMAC (74 mL) was held at 120° C. for 4 hours under nitrogen, cooled, and poured into water. The separated solids were collected, and crystallized from a mixture of toluene and heptane to get the product, 10.17 g (85% yield), m.p. 223-225° C. Additional 1.1 g (9% yield) of the product was recovered after chromatography of the crystallization liquor on silica gel, elution with 2.5% ethyl-acetate-toluene mixture, and crystallization. A sample for analysis was prepared by two successive recrystallizations from toluene, m.p. 225.7-226.5° C. Mass spec: m/z 796 (M$^+$). Anal. Calcd for C$_{48}$H$_{36}$N$_4$O$_6$S: C, 72.35%; H, 4.55%; N, 7.03%; S, 4.02%. Found: C, 72.63%; H, 4.65%; N, 7.11%; S, 4.05%. $^1$H NMR (CDCl$_3$) δ ppm: 0.40 (t, 6H, 7.6 Hz), 1.94-2.08 (m, 2H), 2.10-2.17 (m, 2H), 7.02-7.13 (m, 10H), 7.20-7.26 (m, 4H), 7.38 (t, 1H, 7.4 Hz), 7.50 (t, 1H, 7.4 Hz), 7.71 (d, 2H, 7.92 Hz), 7.91 (d, 1H, 7.92 Hz), 8.03 (d, 1H, 8.0 Hz), 8.07-8.11 (m, 2H), 8.23 (d, 4H, 9.16 Hz). $^{13}$C NMR (CDCl$_3$) δ ppm: 8.64, 32.63, 56.48 (3 sp$^3$C), 116.33, 119.01, 119.57, 121.31, 121.53, 121.56, 122.99, 123.41, 125.06, 125.41, 125.99, 126.33, 127.36, 131.88, 134.95, 136.14, 142.66, 144.06, 145.07, 147.55, 149.92, 150.71, 152.46, 152.24, 163.45, and 168.64 (26 sp$^2$C).

EXAMPLE 12

N,N-Di[4-(4-aminophenoxy)phenyl]-7-(benzothiazol-2-yl)-9,9-diethyl-fluoren-2-amine To a mixture of N,N-di[4-(4-nitrophenoxy)phenyl)]-7-(benzothiazol-2-yl)-9,9-diethyl-fluoren-2-amine (Example 11; 5.25 g, 6.6 mmol), DMAC (75 mL), ethanol (50 mL), and 10% palladium on charcoal catalyst (0.51 g) heated to 70° C., a mixture of hydrazine hydrate (4.9 mL), and ethanol (7 mL) was added in portions over 15 minutes. After two hours at 75° C., the mixture was cooled and poured into water. The separated solids were collected, and transferred to a column of silica gel. Elution with 3:1 toluene-ethyl-acetate mixture gave the product, 2.61 g (54% yield), m.p. 192-194° C. Recrystallization from a mixture of ethyl acetate and hexanes did not raise the m.p. Mass spec: m/z 736 (M$^+$). Anal. Calcd. for C$_{48}$H$_{40}$N$_4$O$_2$S: C, 78.23%; H, 5.47%; N, 7.60%; S, 4.35%. Found: C, 78.23%; H, 5.56%; N, 7.55%; S, 4.41%. $^1$H NMR (CDCl$_3$) δ ppm: 0.37 (t, 6H, 7.32 Hz), 1.88-1.97 (m, 2H), 2.03-2.11 (m, 2H), 3.57 (s, 4H), 6.64-6.73 (m, 4H), 6.85-6.92

(m, 8H), 6.94-6.98 (m, 1H), 7.00-7.10 (m, 5H), 7.36 (t, 1H, 8.16 Hz), 7.48 (t, 1H, 7.12 Hz), 7.55 (d, 1H, 8.28 Hz), 7.65 (m, 1H, 7.92 Hz), 7.89 (m, 1H, 7.6 Hz), 7.99 (dd, 1H, 1.6 and 7.92 Hz), 8.02-8.10 (m, 2H). $^{13}$C NMR (CDCl$_3$) δ ppm: 8.58, 32.59, 56.29 (3 sp$^3$C), 116.19, 116.64, 118.16, 119.09, 120.79, 120.84, 121.26, 121.37, 121.49, 122.86, 124.87, 125.81, 126.21, 127.22, 131.13, 134.12, 134.88, 142.36, 142.55, 144.64, 148.67, 148.86, 150.51, 152.06, 154.23, 154.53, and 168.90 (27 sp$^2$C).

Having thus described exemplary embodiments of the present invention, it should be noted by those skilled in the art that the disclosures herein are exemplary only and that alternatives, adaptations and modifications may be made within the scope of the present invention.

We claim:

1. A chromophore of the formula:

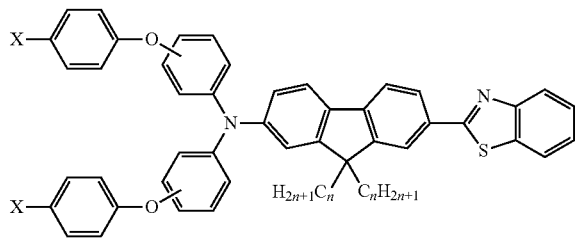

wherein each X-substituted phenoxy group is fixed substituted in the meta position, X=NO$_2$, and C$_n$H$_{2n+1}$ is a straight alkyl chain wherein n is 2.

2. A chromophore of the formula:

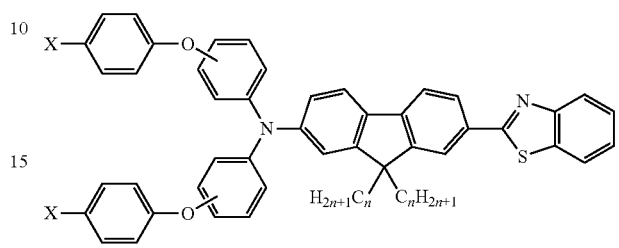

wherein each X-substituted phenoxy group is fixed substituted in the meta position, X=NH$_2$, and C$_n$H$_{2n+1}$ is a straight alkyl chain wherein n is 2.

* * * * *